(12) United States Patent  
Felix et al.

(10) Patent No.: US 8,192,467 B2
(45) Date of Patent: Jun. 5, 2012

(54) CROSS CONNECTOR

(75) Inventors: Brent A. Felix, Sandy, UT (US);
Christian L. Lauridsen, Woodland Hills, UT (US)

(73) Assignee: Innovasis, Inc., Salt Lake City, UT (US)

( * ) Notice: Subject to any disclaimer, the term of this patent is extended or adjusted under 35 U.S.C. 154(b) by 448 days.

(21) Appl. No.: 12/270,597

(22) Filed: Nov. 13, 2008

(65) Prior Publication Data

US 2009/0326588 A1 Dec. 31, 2009

Related U.S. Application Data

(60) Provisional application No. 61/076,510, filed on Jun. 27, 2008.

(51) Int. Cl.
*A61B 17/70* (2006.01)
(52) U.S. Cl. .......................... 606/250; 606/277
(58) Field of Classification Search .............. 606/246, 606/250–253, 27, 277, 278
See application file for complete search history.

(56) References Cited

U.S. PATENT DOCUMENTS

| | | |
|---|---|---|
| 5,474,555 A | 12/1995 | Puno et al. |
| 6,179,838 B1 * | 1/2001 | Fiz ................................ 606/278 |
| 7,207,992 B2 * | 4/2007 | Ritland ......................... 606/86 A |
| 7,666,210 B2 * | 2/2010 | Franck et al. .................. 606/250 |
| 2005/0228377 A1 * | 10/2005 | Chao et al. ........................ 606/61 |
| 2006/0217718 A1 * | 9/2006 | Chervitz et al. ................. 606/61 |
| 2006/0229616 A1 * | 10/2006 | Albert et al. ..................... 606/61 |
| 2007/0213715 A1 * | 9/2007 | Bridwell et al. ................. 606/61 |
| 2008/0281361 A1 * | 11/2008 | Vittur et al. .................... 606/249 |
| 2010/0121379 A1 * | 5/2010 | Edmond ......................... 606/249 |
| 2010/0241168 A1 * | 9/2010 | Franck et al. .................. 606/250 |

OTHER PUBLICATIONS

EBI Spine Systems, EBI Ωmega21 Spinal Fixation System, *Surgical Technique*, published atleast as early as Sep. 1, 2006.
Click'X Top Loading System, *Technique Guide*, Synthes Spine 2003.
Synergy IQ, *Low Back Surgical Technique*, Interpore Cross International, 2003.

* cited by examiner

*Primary Examiner* — Eduardo C Robert
*Assistant Examiner* — Ellen C. Hammond
(74) *Attorney, Agent, or Firm* — Workman Nydegger

(57) ABSTRACT

A cross connector that can be used with a spinal implant includes a first rod clamp having a first end and an opposing second end, the first rod clamp having a first clamp arm crossing a second clamp arm so as to form a scissor coupling. The cross connector also includes a second rod clamp and a cross bar assembly extending between the first rod clamp and the second rod clamp.

24 Claims, 6 Drawing Sheets

CROSS CONNECTOR

CROSS-REFERENCE TO RELATED APPLICATIONS

This application claims the benefit of U.S. Provisional Application Ser. No. 61/076,510, filed Jun. 27, 2008, which application is incorporated herein by specific reference.

BACKGROUND OF THE INVENTION

1. The Field of the Invention

The present invention relates to cross connectors for use in association with spine stabilizing systems and, more specifically, for connecting together adjacent rods of spine stabilizing systems.

2. The Relevant Technology

Various spinal stabilizing systems are available for adjusting or fixing adjacent vertebrae of the spine relative to each other. For example, such systems can be used when it is necessary to fuse together two adjacent vertebrae. In conventional procedures, adjacent vertebrae are stabilized by securing a first pair of polyaxial screws to a first vertebrae. One of the polyaxial screws is secured on the lateral side of the vertebrae while the other of the polyaxial screws is positioned on the medial side of the vertebrae. A second pair of polyaxial screws is then secured to an adjacent vertebrae on the lateral and medial side thereof. As needed, additional pairs of polyaxial screws can be secured on the lateral and medial side of further consecutive vertebrae.

Once the polyaxial screws are positioned, an elongated first rod is secured to each of the polyaxial screws on the lateral side while an elongated second rod is secured to each of the polyaxial screws on the medial side. The rods help to secure each of the vertebrae in a fixed location relative to the others. To help stabilize lateral movement of the vertebrae, a plurality of cross connectors can be connected between the first rod and the second rod at spaced apart locations along the length of the rods. Although conventional cross connectors are effective, they often have a rigid structure making them difficult to install, difficult to adjust, and/or difficult to secure in place.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
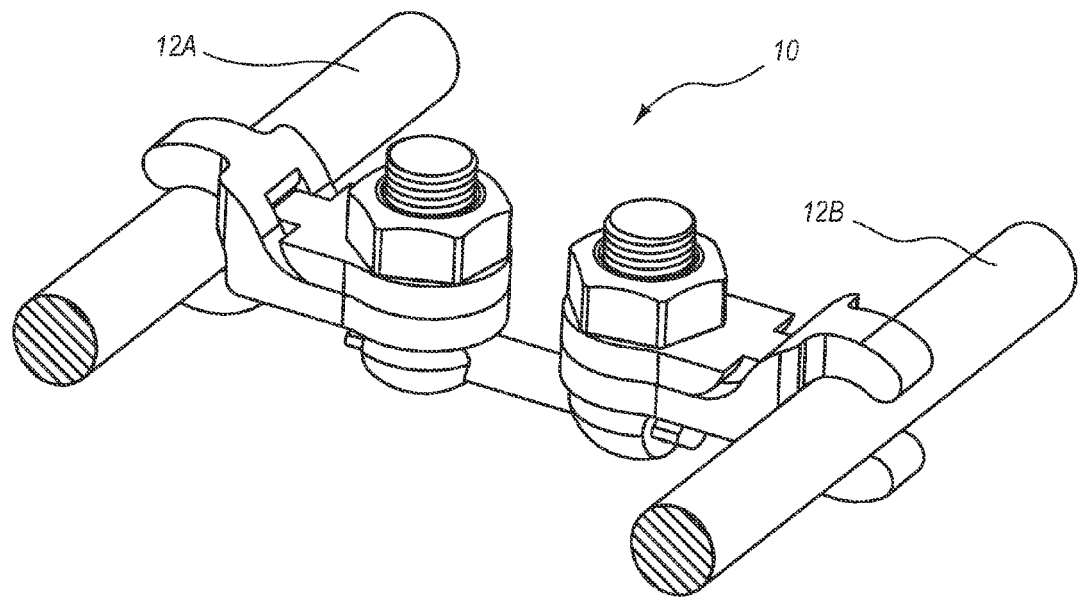
FIG. 1 is a perspective view of a cross connector coupled with a pair of rods.

Depicted in FIG. 1 is one embodiment of a cross connector 10 incorporating features of the present invention. Cross connector 10 is shown being used in association with a first rod 12A and an opposing second rod 12B. It is appreciated that rods 12A and 12B can in turn be connected to a series of pedicle screws, polyaxial screws, or other fasteners that are mounted on adjacent vertebrae of the spine. Cross connector 10 functions to secure rods 12A and 12B relative to each other, thereby securing the adjacent vertebrae relative to each other. In view of the forgoing, cross connector 10 can function as part of a spinal implant or spine stabilizing system.

In alternative embodiments, however, it is appreciated that cross connector 10 need not be used in association with the spine but can be used in other procedures where it is necessary to stabilize adjacent rods. It is also appreciated that cross connector 10 can be used in association with a variety of different spine stabilizing systems. By way of example and not by limitation, cross connector 10 can be used in association with the spine stabilizing systems disclosed in U.S. patent application Ser. No. 61/053,545, filed on May 15, 2008 and U.S. patent application Ser. No. 11/863,133, filed on Sep. 27, 2007, both of which are hereby incorporated by reference, and can also be used with other conventional spine stabilizing systems.

Figure 2:
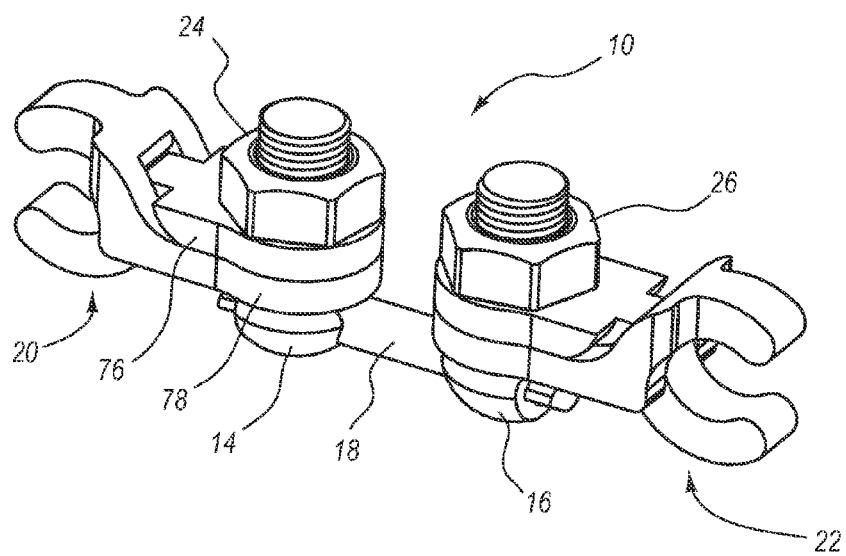
FIG. 2 is a perspective view of the cross connector shown in FIG. 1.

As depicted in FIG. 2, cross connector 10 comprises a first fastener 14, a second fastener 16 and a cross bar 18 extending therebetween. A first rod clamp 20 is mounted on first fastener 14 while a second rod clamp 22 is mounted on second fastener 16. In the depicted embodiment, a first nut 24 is used to secure first rod clamp 20 on first fastener 14 while a second nut 26 is used to secure second rod clamp 22 on second fastener 16. Each of the components of cross connector 10 are typically comprised of a medical grade implantable material which is usually a metal such as titanium or stainless steel. Other medical grade implantable materials can also be used. The above referenced structural elements will now be discussed in greater detail.

Figure 3:
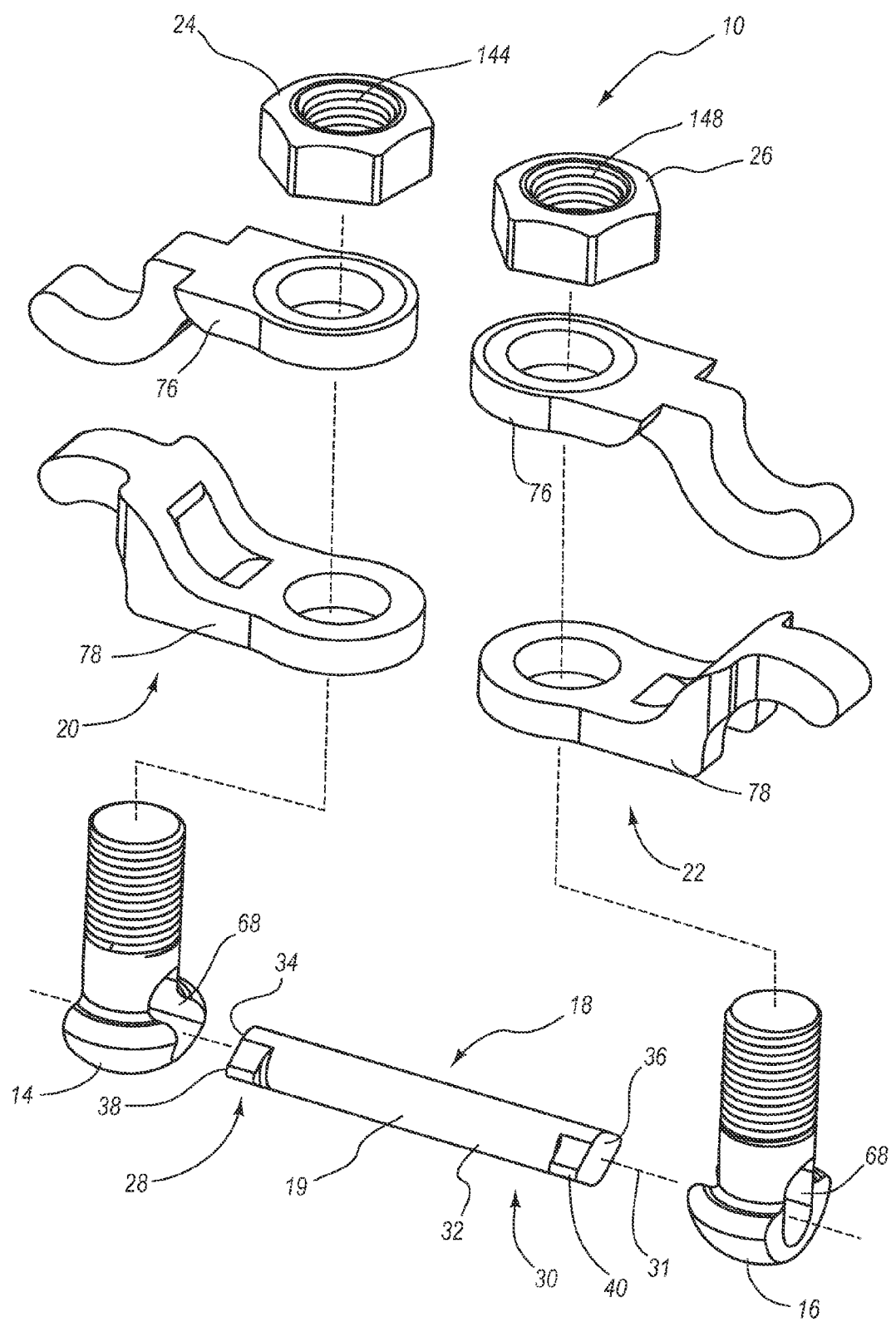
FIG. 3 is an exploded perspective view of the cross connector shown in FIG. 2.

As depicted in FIG. 3, cross bar 18 comprises of an elongated rod 19 having a central longitudinal axis 31 and an exterior surface 32 that each extend between a first end 28 and an opposing second end 30. In the embodiment depicted, rod 19 has an elongated transverse cross section wherein the width thereof is greater than the height thereof. For example, in the depicted embodiment, rod 19 has a substantially elliptical transverse cross section. In alternative embodiments, however, it is appreciated that the transverse cross section of rod 19 can be other elongated configurations or need not be elongated. For example, other transverse cross sectional configurations that can be used include circular, triangular, rectangular, and other polygonal or irregular configurations.

Figure 4:
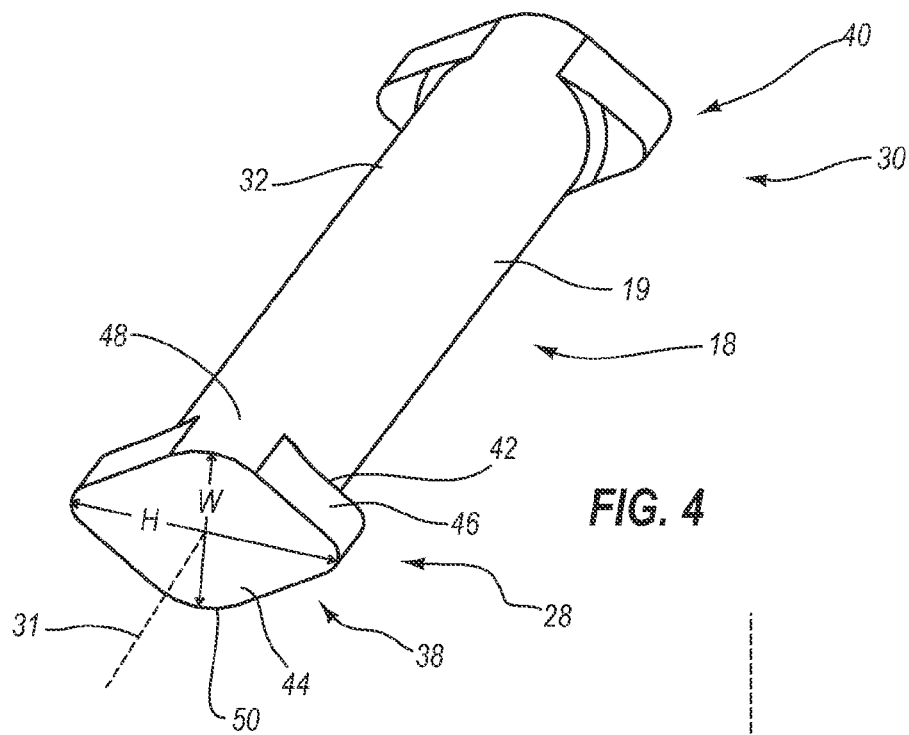
FIG. 4 is a perspective view of the cross bar shown in FIG. 3.

Cross bar 18 further comprises an enlarged first stop 38 formed on first end 28 of rod 19 and an enlarged second stop 40 located at second end 30 of rod 19. Turning to FIG. 4, first stop 38 has an inside face 42, an opposing outside face 44, and a side face 46 extending therebetween. Although not required, inside face 42 and outside face 44 are shown substantially disposed in parallel planes that are orthogonal to central longitudinal axis 31. First stop 38 has a transverse cross sectional configuration that is normal to central longitudinal axis 31 and that is elongated. Specifically, the transverse cross sectional configuration of first stop 38 has a maximum height H that is longer than the maximum width W thereof. In the depicted embodiment, the transverse cross sectional configuration of first stop 38 has a substantially diamond shaped configuration with rounded corners. In alternative embodiments, however, the transverse cross sectional configuration of first stop 38 can be elliptical, rectangular, triangular or any other polygonal, non-polygonal or irregular elongated configuration.

For reasons as will be discussed below in greater detail, the transverse cross section of first stop 38 has an area and/or maximum diameter that is greater than that of the transverse cross section of rod 19. For example, the maximum width W of stop 38 is equal to the maximum width of rod 19 but the maximum height H of stop 38 is greater than the maximum height of rod 19. As a result of stop 38 and rod 19 each having the same maximum width, cross bar 18 has a two opposing, flat, biasing surfaces 48 and 50 that extend along the entire length thereof. Second stop 40 is identical to first stop 38 and thus like reference characters are used to identify like elements between first stop 38 and second stop 40. Cross bar 18 can come in a variety of different lengths that are typically in a range between about 20 mm to about 60 mm with examples of different lengths being 20 mm, 30 mm, 40 mm, 50 mm and 60 mm each being ±2 mm.

Figure 5:
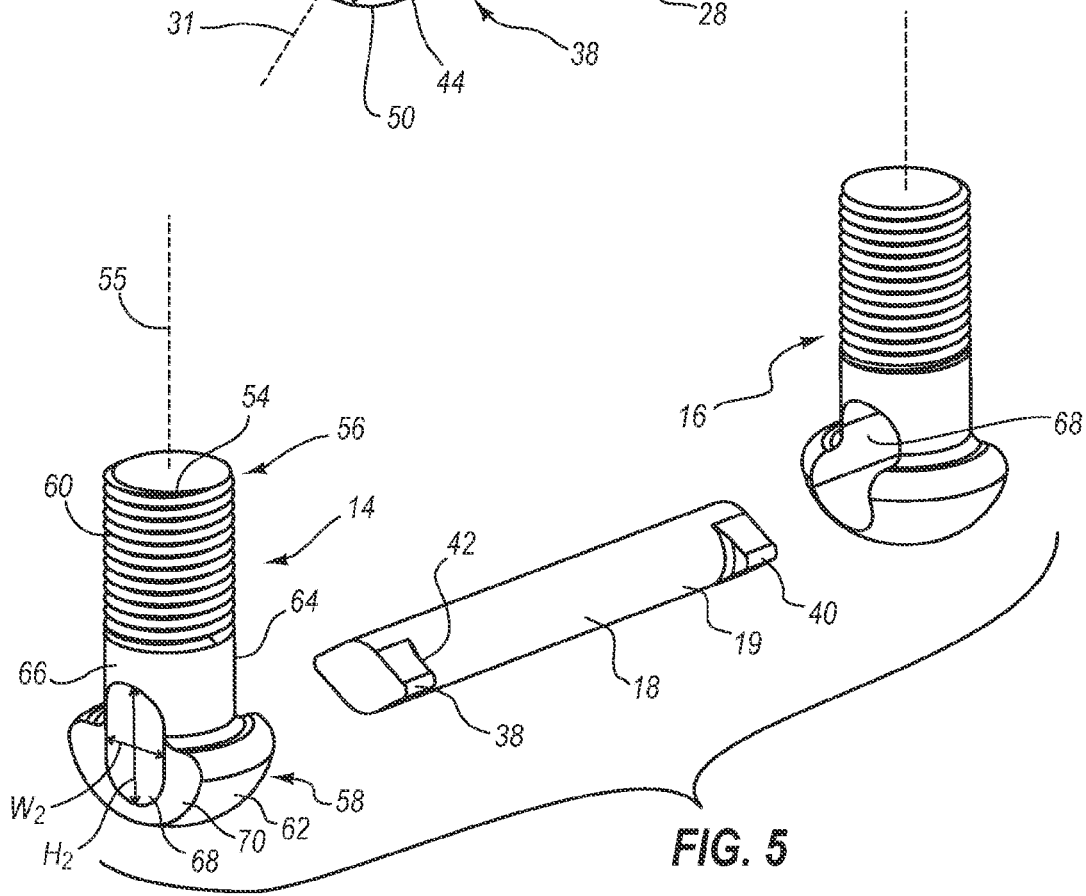
FIG. 5 is a perspective view of the cross bar and fasteners shown in FIG. 3.

Turning to FIG. 5, first fastener 14 is elongated and has a central longitudinal axis 55 extending between a first end 56 and an opposing second end 58. First fastener 14 comprises an elongated shaft 54 that is substantially cylindrical and that generally extends between first end 56 and opposing second end 58. Helical threads 60 are formed on and encircle at least a portion of first end 56 of shaft 54. An enlarged head 62 is formed on second end 58 of shaft 54 and radially outwardly projects therefrom. First fastener 14 has a first side 64 and an opposing second side 66. A passage 68 transversely extends through second end 58 of first fastener 14 between first side 64 and opposing second side 66. Head 62 is cut away on second side 66 so as to form a substantially flat engagement face 70 that is flushed with and partially encircles the opening to passage 68 at second side 66. Passage 68 has an elongated transverse cross sectional configuration. Specifically, the transverse cross sectional configuration of passage 68 has a maximum height $H_2$ that is longer than a maximum with $W_2$ thereof.

In the embodiment depicted, passage 68 is bounded by a pair of opposing parallel sidewalls that intersect at opposing rounded end walls. In alternative embodiments, it is appreciated that the transverse cross sectional configuration of passage 68 can be oval, elliptical, diamond, rumpus, or any other desired elongated figuration. However, passage 68 is configured so that first stop 38 can pass therethrough when properly aligned. To enable the passage of first stop 38, the maximum height and width of passage 68 are typically slightly larger then the maximum height and width first stop 38 and is configured so that when the height of first stop 38 is aligned with the height of passage 68, first stop 38 of cross bar 18 can freely pass through passage 68 from first side 64 to second side 66.

Figure 6:
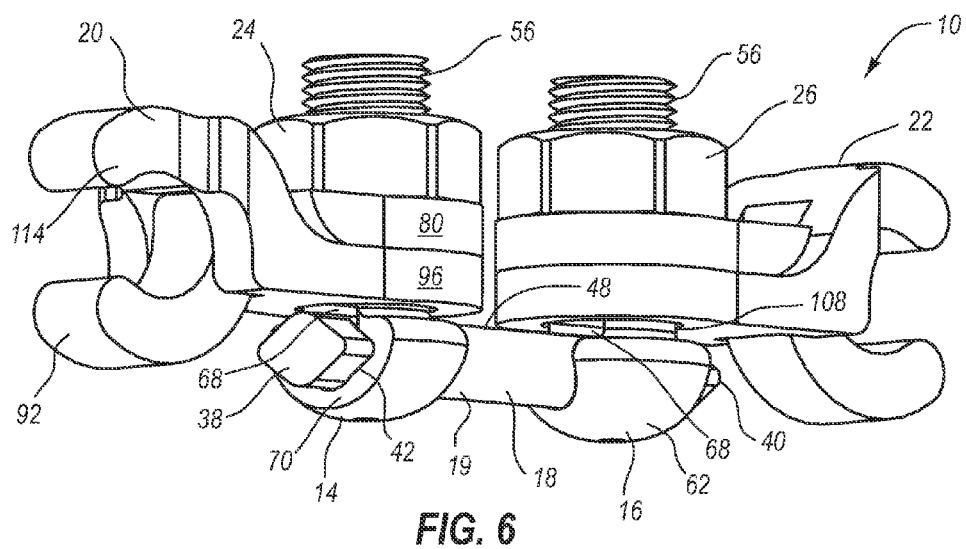
FIG. 6 is a bottom perspective view of the cross connector shown in FIG. 2.

Once first stop 38 has passed through passage 68, cross bar 18 is rotated 90° as depicted in FIG. 6. Maximum height H of first stop 38 (FIG. 4) is longer than maximum width $W_2$ of passage 68 (FIG. 5). As such, inside face 42 of stop 38 biases against engagement face 70 of first fastener 14 so as to prevent stop 38 from being pulled back out through passage 68.

Second fastener 16 has the same configuration to first fastener 14 and interacts with second stop 40 in the same manner as discussed above. As such, like elements between fasteners 14 and 16 are identified by like reference characters.

It is appreciated that fasteners 14 and 16 can come in a variety of different configurations. For example, enlarged head 62 of fastener 14 functions in part to increase the structural strength of fastener 14 thereat. In an alternative embodiment head 62 can be eliminated such as by increasing the diameter of shaft 54 along the entire length thereof.

Figure 7:
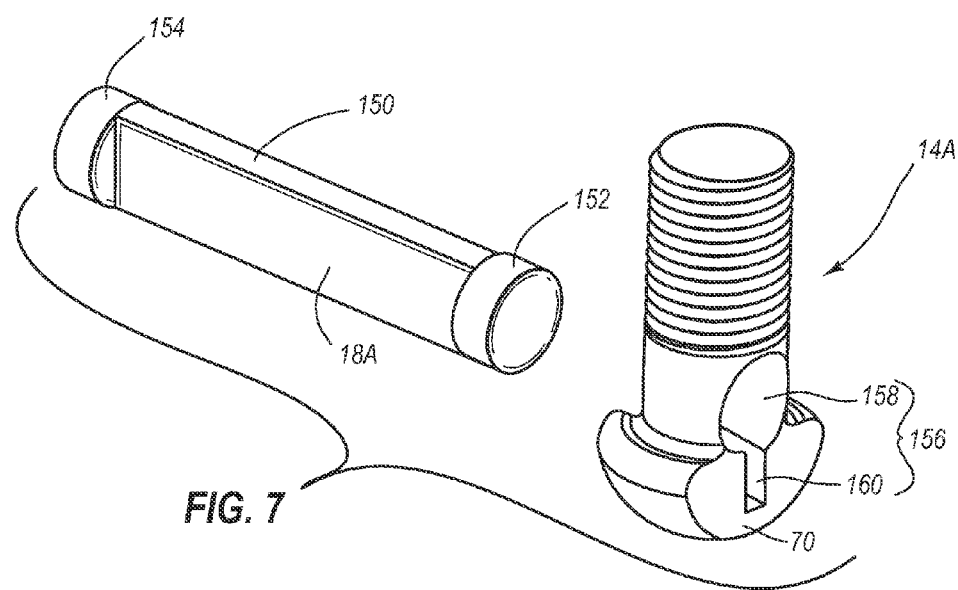
FIG. 7 is a perspective view of an alternative embodiment of a cross bar and fastener.

Depicted in FIG. 7 is an alternative embodiment of a cross bar 18A that can be used with an alternative embodiment of a fastener 14A. Cross bar 18A comprises a rod 150 having an enlarged first stop 152 positioned at one end thereof and enlarged second stop 154 positioned at the opposing end thereof. In this embodiment, each stop 152 and 154 has a substantially circular transverse cross section. Rod 150 has a substantially rectangular transverse cross section with rounded sides that extend to the perimeter of stops 152 and 154. As such, rod 150 and stops 152/154 have the same maximum width so as to produce a uniform flat surface along opposing sides of cross bar 15A but stops 152/154 have a maximum height orthogonal to the width that is greater than the maximum height of rod 150.

Fastener 14A has substantially the same configuration as fastener 14 and thus like elements are identified by like reference characters. In contrast to fastener 14, however, fastener 14A has a passage 156 that transversely extends therethrough. Passage 156 comprises a first passage portion 158 extending through fastener 14A that is sized so that first stop 152 can pass therethrough. Passage 156 also comprises a second passage portion 160 that transversely extends through fastener 14A and communicates with first passage portion 158. Second passage portion 160 is constricted relative to first passage portion 158 and is sized so that first stop 152 cannot pass therethrough but that rod 150 can be received therein. As a result, first stop 152 can be passed through passage 158 following which rod 150 is received within second passage portion 160. First stop 152 then biases against engagement face 70 of fastener 14A and is precluded from passing back through passage 156. A corresponding second fastener 14A is used at the second end of cross bar 18A in like manner.

Figure 8:
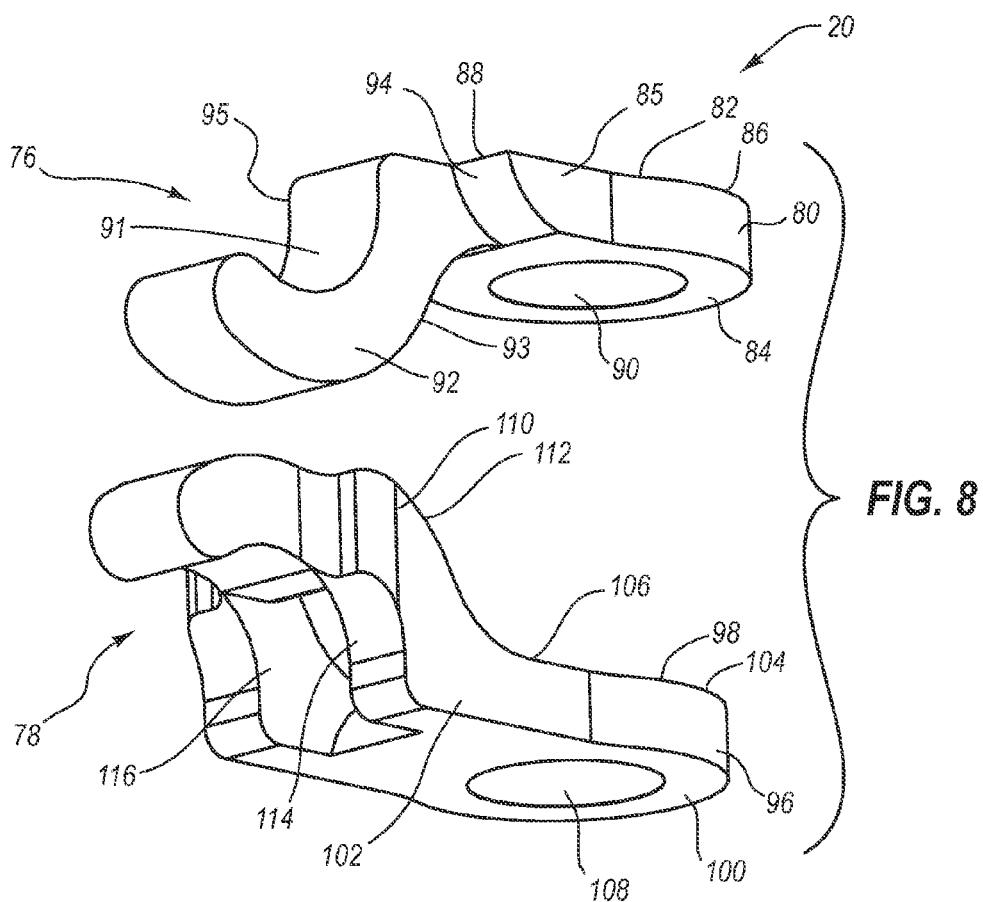
FIG. 8 is an exploded perspective view of the rod clamp shown in FIG. 2.

Returning to FIG. 2, first rod clamp 20 comprises a first clamp arm 76 and a second clamp arm 78. As depicted in FIG. 8, first clamp arm 76 comprises a plate 80 having a top surface 82 and an opposing bottom surface 84 that extend between a first end 86 and an opposing second end 88 and that has a side surface 85 extending therebetween. An opening 90 extends through plate 80 between opposing surfaces 82 and 84. Opening 90 is configured to enable first end 56 of first fastener 14 (FIG. 5) to pass therethrough. An arm 92 having a generally U-shaped configuration downwardly and outwardly projects from side surface 85 at second end 88 of plate 80. Arm 92 has an interior surface 91 having a substantially U-shaped contour and an opposing exterior surface 93. Curved ramps 94 and 95 are formed on side surface 85 of plate 80 on opposing sides of arm 92.

Similarly, second clamp arm 78 comprises a plate 96 having a top surface 98 and an opposing bottom surface 100 that extend between a first end 104 and an opposing second end 106 with a side surface 102 extending therebetween. Again, an opening 108 extends through plate 96 between opposing surfaces 98 and 100. Opening 108 is also configured to enable first end 56 of first fastener 14 (FIG. 5) to pass therethrough. An arm 110 having a substantially U-shaped configuration and inverted relative to arm 82 projects upwardly and outwardly from second end 106 of plate 96. Arm 110 has an exterior surface 112 and an opposing interior surface 114, interior surface 114 having a substantially U-shaped configuration. A passage 116 extends through arm 110 between surfaces 112 and 114 adjacent to second end 106 of plate 96. Passage 116 is configured to allow arm 92 to pass therethrough.

Figure 9:
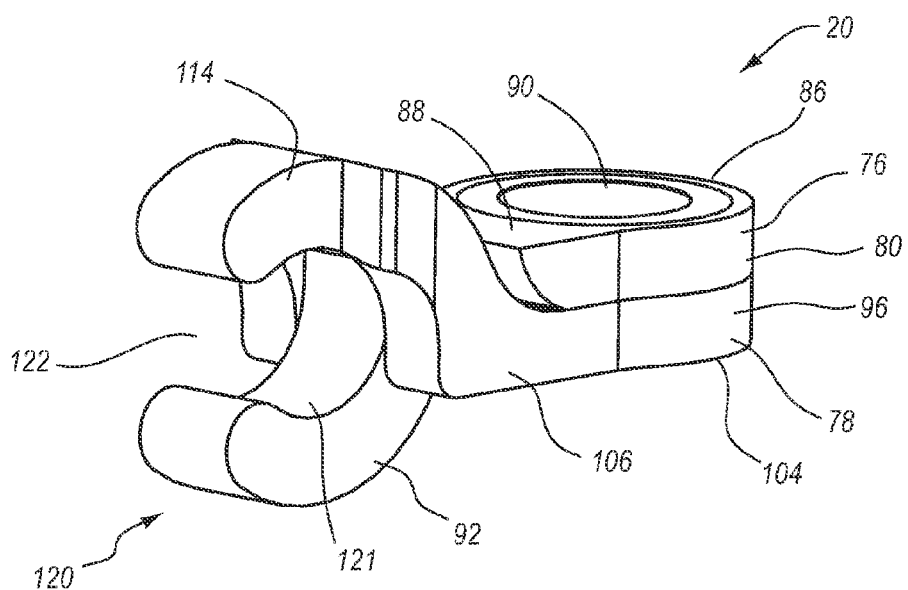
FIG. 9 is a perspective view of the assembled rod clamp shown in FIG. 8.

Clamp arms 76 and 78 are designed to nest together as depicted in FIG. 9 with arm 92 of first clamp arm 76 being received within passage 116 of second clamp arm 78 so that plates 80 and 96 rest against each other. In this configuration, openings 90 and 108 of first rod clamp 20 are aligned. Furthermore, first clamp arm 76 crosses second clamp arm 78 at a location between the opposing ends thereof so as to form a scissor coupling. That is, clamp arms 76 and 78 pivot relative to each other in the same general fashion as scissors. Specifically, as the first end of plates 80 and 96 are separated, a central portion of clamp arm 76 pivots on a central portion of clamp arm 78 causing arms 92 and 114 to likewise separate. As plates 80 and 96 are brought back together, arms 92 and 114 are also brought back together.

In the coupled configuration, arms 92 and 114 combine to form a locking jaw 120 having a mouth 121 formed therebetween. A gap 122 is formed between the terminal ends of arms 92 and 114 that provides access to mouth 121. Locking jaw 120 is configured to lock a rod 12A (FIG. 1) within mouth 121. That is, by separating first ends 86 and 104 of plates 80 and 96 while generally retaining together second ends 88 and 106 thereof, mouth 121 of jaw 120 is widened as discussed above. Once mouth 120 is widened, rod 12A can be positioned within mouth 121 between arms 92 and 114. Plates 80 and 96 can then be pressed back together causing arms 92 and 114 to bias against or clamp on opposing sides of rod 12A and thereby lock rod 12A in place. The U-shaped contour of the interior surface of arms 92 and 114 can be generally complimentarily to the diameter of rod 12A to facilitate capturing of rod 12A between the arms.

Figure 10:
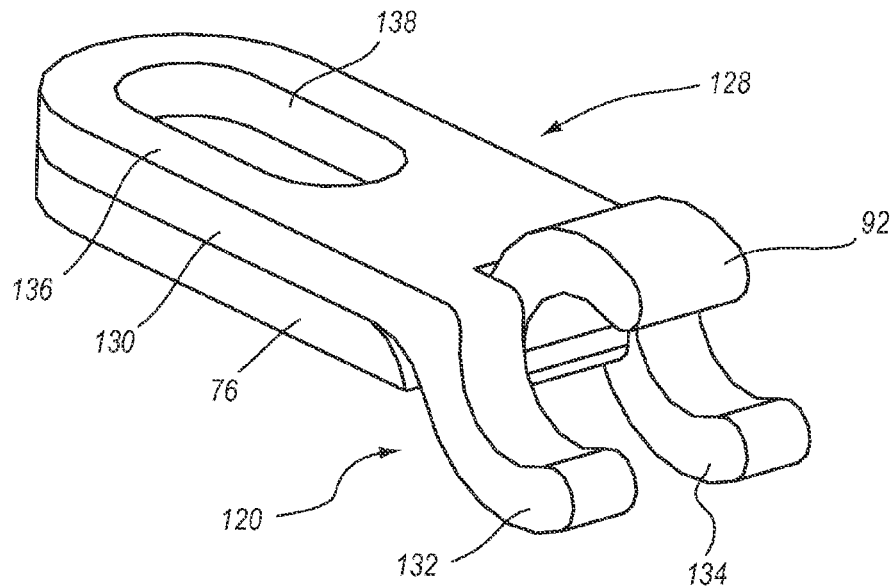
FIG. 10 is a perspective view of an assembled alternative embodiment of a rod clamp.
Figure 11:
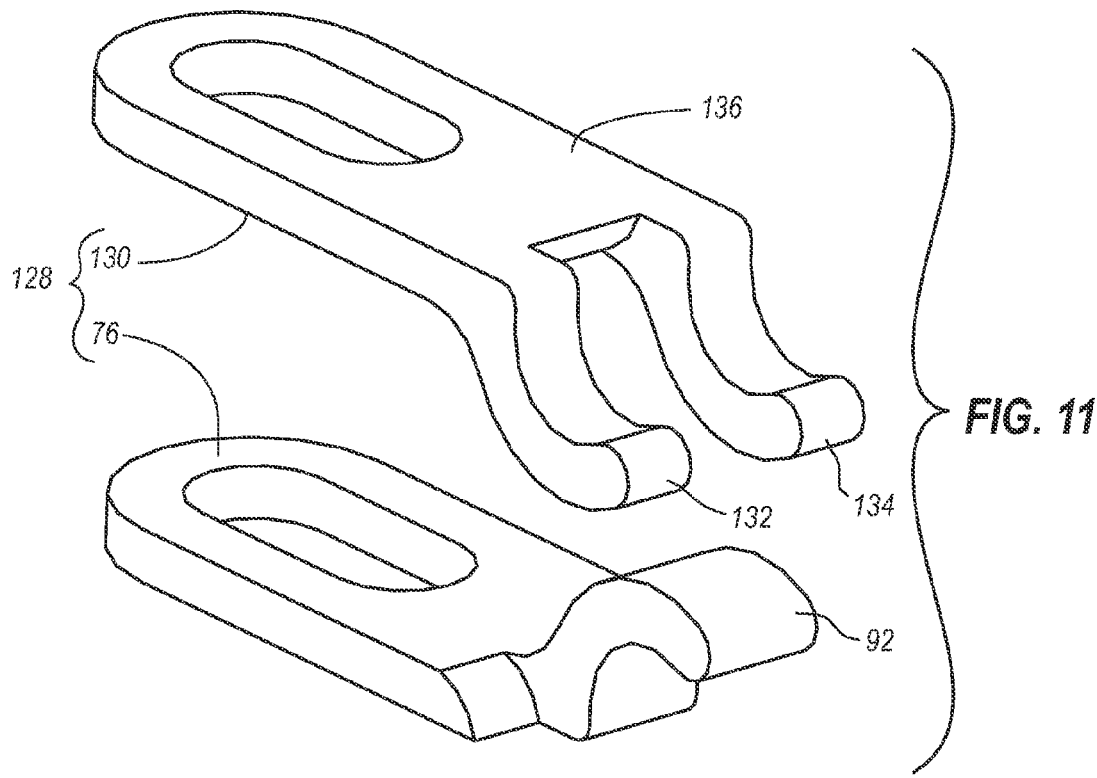
FIG. 11 is an exploded view of the rod clamp shown in FIG. 10.

It is appreciated that first rod clamp 20 can come in a variety of different configurations. For example, depicted in FIGS. 10 and 11 is one alternative embodiment of a rod clamp 128. Like elements between rod clamps 128 and 20 are identified by like reference characters. Rod clamp 128 comprises first clamp arm 76 and a second clamp arm 130 that are coupled together in a scissor coupling. Second clamp arm 130 is similar to second clamp arm 78. However, in contrast to having a single arm with a passage extending therethrough, second clamp arm 130 comprises a pair of spaced apart substantially U-shaped arms 132 and 134 that project from plate 136 of second clamp arm 130.

Again, clamp arms 76 and 130 are mounted together in a scissor coupling with arm 92 of first clamp arm 76 being position between arms 132 and 134 of second clamp arm 130. This configurations allows select opening and closing of the locking jaw 120 bounded by arms 132/134 and 92 as clamp arms 76 and 130 are pivoted. Also shown in this embodiment, each clamp arm 76 and 130 has an elongated opening 138 extending therethrough that are in alignment. The elongated openings 138 permit further adjustment of the location of rod clamp 128 relative to fastener 14. It is appreciated that other clamping configurations can also be used.

Returning to FIG. 2, second rod clamp 22 is depicted as being substantially identical to first rod clamp 20. As such, the above discussion with regard to first rod clamp 20 is also applicable to second rod clamp 22 with like elements being identified by like reference characters. If desired, in alternative embodiments first rod clamp 20 and second rod clamp 22 can have different configurations.

Connector assembly 10 is typically fully assembled in a loose state prior to use. Specifically, during assembly a cross bar 18, as shown in FIG. 5, is selected having a desired length. The opposing ends of cross bar 18 are aligned with and passed through passage 68 of first fastener 14 and second fastener 16, respectively. Once inserted, cross bar 18 is rotated 90° so as to prevent unwanted separation between cross bar 18 and fasteners 14 and 16 as previously discussed.

Next, as depicted in FIG. 6, with rod clamps 20 and 22 in their assembled scissor coupling, first end 56 of fasteners 14 and 16 are advanced through the aligned openings 90 and 108 (FIG. 8) of rod clamps 20 and 22, respectively. Rod clamps 20 and 22 are advanced down along fasteners 14 and 16 until they come to rest on biasing surface 48 of cross bar 18. Each rod clamp 20 and 22 can bias against biasing surface 48 on each opposing side of each fastener 14 and 16. It is noted that as rod clamps 20 and 22 are advanced onto fasteners 14 and 16, rod clamps 20 and 22 cover a portion of each passage 68. As such, the diameter of each passage 68 is effectively reduced thereby preventing the unintentional removal of cross bar 18 even if cross bar 18 was again rotated back 90°. Furthermore, because rod clamps 20 and 22 are resting against cross bar 18, rod clamps 20 and 22 can bias directly against stops 38 and 40 and prevent the rotation thereof.

Next, nut 24 having a threaded bore 144 (FIG. 3) extending therethrough is threaded onto first end 56 of fastener 14. As a result, first rod clamp 20 is captured on first fastener 14 between cross bar 18 and nut 24. Similarly, nut 26 having a threaded bore 148 (FIG. 3) is threaded onto first end 56 of fastener 16 so as to capture second rod clamp 22 on first fastener 14 between cross bar 18 and nut 26.

With nuts 24 and 26 loosely threaded onto fasteners 14 and 16, fasteners 14 and 16 are still free to slide along cross bar 18. For example, stop 38 can move between biasing against fastener 14 and biasing against arm 92 of rod clamp 20. Rod clamps 20 and 22 are also free to rotate about fasteners 14 and 16. Furthermore, where nuts 24 and 26 are not biasing against rod clamps 20 and 22, respectively, the locking jaws of rod clamps 20 and 22 can be freely expanded and contracted a small amount. In this loosely assembled configuration, cross connector 10 can then be coupled to rods 12A and 12B (FIG. 1) which are already fixed to the patient. That is, without removing nuts 24 and 26 but by adjusting their position on fasteners 14 and 16, rods 12A and 12B can be either freely positioned within or snap-fit into the locking jaws of rod clamps 20 and 22. In one embodiment it is desirable that when rod 12A is received within the locking jaw of rod clamp 20, rod 12A widens the locking jaw so that plates 80 and 96 are separated at first end thereof. This enables the locking jaw to better clamp down onto rod 12A when plates 80 and 96 are pressed together.

The free movement of fasteners 14 and 16 along cross bar 18 enables cross connector 10 to expand or contact so that a single cross connector 10 can be used to couple to rods 12A and 12B at a variety of different spacings. For example in one embodiment cross connector 10 is able to lengthen and contract over a distance in a range between 5 mm to about 15 mm with at least 10 mm being common. Other dimension can also be used.

Once cross connector 10 is coupled with rods 12A and 12B and properly positioned, a driver is used to tighten nut 24 on fastener 14. In so doing, plates 80 and 96 of rod clamp 20 are pressed together between nut 24 and cross bar 18 so that arms 92 and 114 of rod clamp 20 tightly clamp onto rod 12A. Likewise, the biasing of rod clamp 20 against cross rod 18 prevents further rotation of rod clamp 20 about fastener 14 and prevents fastener 14 from further moving along cross bar 18. Tightening nut 26 on fastener 16 similarly clamps rod clamp 22 on rod 12B, locks rod clamp 22 on fastener 16, and locks fastener 16 relative to cross rod 18. As a results, cross connector 10 securely locks rod 12A to rod 12B.

The different features of the above discussed embodiments of the present invention provide unique advantages. By way of example and not by limitation, the ability of cross connector 10 to expand and contract by enabling fasteners 14 and 16 to move relative to cross bar 18 enables a singe cross connector 10 to be used in a larger number of situations where different sizes are required. However, in alternative embodiments, cross bar 18 can be rigidly connected to one or both of fasteners 14 and 16 such as by welding or being integrally formed therewith.

The ability to rotate rod clamps 20 and 22 about the fasteners is also beneficial in that it permits rod clamps 20 and 22 to be rotated out of the way during initial placement between rods 12A and 12B. Rod clamps 20 and 22 can then be rotated back into alignment when coupling with rods 12A and 12B. The ability to rotate rod clamps 20 and 22 also facilitates easier connection to rods 12A and 12B when the rods are bent. However, in alternative embodiments one or both of rod clamps 20 and 22 can be fixed to the fasteners so that they cannot rotate relative to the fasteners.

Finally, the scissor coupling of rod clamps 20 and 22 also provides unique advantages. By having the scissor coupling, rod clamps 20 and 22 can be easily snap fit in a loose engagement on rods 12A and 12B. This loose engagement between rod clamps 20 and 22 and rods 12A and 12B enables easy manipulation and positioning of cross connector 10 and enables easy tightening of the nuts for locking cross connector 10 in place. In alternative embodiments, it is appreciated that cross connectors can be designed having only one of the above benefits or combinations thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A spinal implant cross connector for connecting a first rod and a spaced apart second rod, the cross connector comprising:
    a first rod clamp comprising:
        a first clamp arm extending longitudinally between a first end and a spaced apart second end; and
        a second clamp arm extending longitudinally between a first end and a spaced apart second end, the first clamp arm crossing the second clamp arm so as to form a scissor coupling having a pivot axis where the first clamp arm crosses the second clamp arm, the first clamp arm being coupled to the second clamp arm at a position spaced apart from the pivot axis, the second ends of the first and second clamp arms bounding a mouth configured to engage a first rod, the pivot axis being positioned between the first and second ends of the first clamp arm and between the first and second ends of the second clamp arm such that:
            pivotal movement of the first ends of the first and second clamp arms towards each other about the pivot axis causes the second ends of the first and second clamp arms to correspondingly rotate about the pivot axis towards each other; and
            pivotal movement of the first ends of the first and second clamp arms away from each other about the pivot axis causes the second ends of the first and second clamp arms to correspondingly rotate about the pivot axis away from each other;
    a second rod clamp configured to engage a second rod; and
    a cross bar assembly extending between the first rod clamp and the second rod clamp without passing through the mouth.

2. The cross connector as recited in claim 1, wherein:
    the first clamp arm comprises a first plate having a substantially U-shaped first arm projecting therefrom; and
    the second clamp arm comprises a second plate having a substantially U-shaped second arm projecting therefrom, the first plate being disposed adjacent to the second plate such that the substantially U-shaped first arm crosses the substantially U-shaped second arm so as to bound the mouth.

3. The cross connector as recited in claim 2, wherein the first clamp arm attaches to the second clamp arm at an attachment location positioned at the first ends of the first, and second clamp arms and the scissor coupling is formed between the mouth and the attachment location.

4. The cross connector as recited in claim 1, wherein the second rod clamp comprises a third clamp arm and a fourth clamp arm, the third clamp arm crossing the fourth clamp arm so as to form a scissor coupling.

5. The cross connector as recited in claim 1, wherein the cross bar assembly comprises:
    an elongated cross bar having a first end and an opposing second end;
    a first fastener removably connecting the first end of the cross bar to the first rod clamp, the first fastener also coupling the first end of the first clamp arm to the first end of the second clamp arm; and
    a second fastener removably connecting the second end of the cross bar to the second rod clamp.

6. The cross connector as recited in claim 5,
    wherein the first rod clamp comprises a passage formed thereon that passes through the first end of the first clamp arm and the first end of the second clamp arm; and
    wherein the first fastener comprises an elongated shaft having a first end and an opposing second end, the first end of the shaft passing through the passage of the first rod clamp.

7. The cross connector as recited in claim 6, wherein at least a portion of the shaft of the first fastener is threaded and a nut is threaded onto the shaft.

8. The cross connector as recited in claim 6, further comprising a passage laterally passing through the first fastener, the first end of the cross bar extending through the passage.

9. The cross connector as recited in claim 8,
    wherein the passage of the first fastener has an elongated transverse cross section; and
    wherein the cross bar comprises a rod having an enlarged first stop formed at a first end of the rod and an enlarged second stop formed at a second end of the rod, the passage of the first fastener being configured so that the first stop can pass therethrough.

10. The cross connector as recited in claim 1, wherein the first rod clamp and the second rod clamp are comprised of a medical grade implantable material.

11. The cross connector as recited in claim 1, wherein the first clamp arm passes through an enclosed passage of the second clamp arm.

12. The cross connector as recited in claim 1, wherein the cross bar assembly comprises a cross bar positioned so that the cross bar and the pivot axis are nonintersecting.

13. The cross connector as recited in claim 1, wherein the cross bar assembly is coupled to the first rod clamp at a position spaced apart from the mouth.

14. A cross connector comprising:
an elongated cross bar having a first end and an opposing second end;
an elongated first fastener comprising an elongated shaft having a first end and an opposing second end, the first fastener bounding a first passage that laterally passes through the first fastener at the second end thereof, the first end of the cross bar passing through the first passage;
an elongated second fastener having a first end and an opposing second end, the second fastener bounding a second passage that laterally passes through the second fastener at the second end thereof, the second end of the cross bar passing through the second passage;
a first rod clamp removably coupled to the first fastener, the first rod clamp comprising a first clamp arm crossing a second clamp arm so as to form a scissor coupling, the first rod clamp having a first end and an opposing second end, the first rod clamp having an opening formed on the first end thereof that passes through the first clamp arm and the second clamp arm, the first end of the shaft passing through the opening of the first rod clamp; and
a second rod clamp removably coupled to the second fastener.

15. The cross connector as recited in claim 14, wherein the passage of the first fastener has an elongated transverse cross section and the first end of the cross bar has an elongated transverse cross section.

16. The cross connector as recited in claim 14, wherein the cross bar comprises:
an elongated rod having a first end and an opposing second end;
an enlarged first stop formed at the first end of the rod; and
an enlarged second stop formed at the second end of the rod.

17. The cross connector as recited in claim 16, wherein the enlarged first stop has an elongated transverse cross section.

18. The cross connector as recited in claim 16, wherein the passage of the first fastener comprises a first passage portion through which the first stop can pass and a second passage portion communicating with the first passage portion through which the first stop cannot pass.

19. The cross connector as recited in claim 14, wherein an enlarged head is formed on the first end of the elongated shaft.

20. The cross connector as recited in claim 14, wherein:
the first clamp arm comprises a first plate having a substantially U-shaped first arm projecting therefrom; and
the second clamp arm comprises a second plate having a substantially U-shaped second arm projecting therefrom, the first plate being disposed adjacent to the second plate with the first arm crossing the second arm, the first arm and second arm bounding a mouth configured to engage a rod.

21. A cross connector comprising:
an elongated cross bar having a first end and an opposing second end;
an elongated first fastener comprising an elongated shaft having a first end and an opposing second end, the first fastener bounding a first passage that laterally passes through the first fastener at the second end thereof, the first end of the cross bar passing through the first passage;
an elongated second fastener having a first end and an opposing second end, the second fastener bounding a second passage that laterally passes through the second fastener at the second end thereof, the second end of the cross bar passing through the second passage;
a first rod clamp removably coupled to the first fastener, the first rod clamp having an opening formed therethrough, the first end of the shaft of the first fastener passing through the opening of the first rod clamp; and
a second rod clamp removably coupled to the second fastener.

22. A spinal implant cross connector comprising:
a first rod clamp having a first end and an opposing second end, a passage being formed on the first end of the first rod clamp that passes therethrough and the second end being configured to receive a rod;
a second rod clamp configured to receive a rod; and
a cross bar assembly extending between the first rod clamp and the second rod clamp, the cross bar assembly comprising:
an elongated cross bar having a first end and an opposing second end;
a first fastener comprising an elongated shaft having a first end and an opposing second end, the first end of the shaft passing through the passage of the first rod clamp, an elongated passage laterally passing through the first fastener, the first end of the cross bar extending through the elongated passage and being secured therein by pressure from the first rod clamp; and
a second fastener removably connecting the second end of the cross bar to the second rod clamp.

23. The cross connector as recited in claim 22, wherein an enlarged head is formed on the second end of the elongated shaft, the elongated passage passing through the enlarged head.

24. The cross connector as recited in claim 22, further comprising a nut that is threaded onto the fastener so as to cause the first rod clamp to pressure the first end of the cross bar thereby securing the first end of the crossbar within the elongated passage.

* * * * *